(12) United States Patent
Furcoiu

(10) Patent No.: US 11,326,731 B2
(45) Date of Patent: May 10, 2022

(54) PIPE REPAIR ASSEMBLY

(71) Applicant: Mueller International, LLC, Atlanta, GA (US)

(72) Inventor: Aurelian Ioan Furcoiu, Chattanooga, TN (US)

(73) Assignee: Mueller International, LLC, Atlanta, GA (US)

( * ) Notice: Subject to any disclaimer, the term of this patent is extended or adjusted under 35 U.S.C. 154(b) by 0 days.

(21) Appl. No.: 16/845,557

(22) Filed: Apr. 10, 2020

(65) Prior Publication Data

US 2020/0340610 A1 Oct. 29, 2020

Related U.S. Application Data

(60) Provisional application No. 62/838,073, filed on Apr. 24, 2019.

(51) Int. Cl.
*A61F 2/95* (2013.01)
*F16L 55/163* (2006.01)

(52) U.S. Cl.
CPC ..... *F16L 55/163* (2013.01); *A61F 2002/9505* (2013.01)

(58) Field of Classification Search
CPC .... A61F 2/95; A61F 2/954; A61F 2002/9505; A61F 2002/9511; A61F 2002/9534; A61F 2/2427; A61F 2/243; A61F 2/2439
See application file for complete search history.

(56) References Cited

U.S. PATENT DOCUMENTS

| | | |
|---|---|---|
| 3,895,652 A | 7/1975 | Zach |
| 4,589,447 A | 5/1986 | Kane et al. |
| 4,647,072 A | 3/1987 | Westman |
| 5,119,862 A | 6/1992 | Maimets et al. |
| 5,351,720 A | 10/1994 | Maimets |
| 6,712,556 B2 | 3/2004 | Penza |
| 6,820,653 B1 | 11/2004 | Schempf et al. |
| 7,025,580 B2 | 4/2006 | Heagy et al. |

(Continued)

FOREIGN PATENT DOCUMENTS

| | | |
|---|---|---|
| EP | 0621015 | 10/1994 |
| JP | 2005278993 | 10/2005 |

(Continued)

OTHER PUBLICATIONS

US 11,035,513 B2, 06/2021, Furcoiu (withdrawn)

(Continued)

*Primary Examiner* — Diane D Yabut
(74) *Attorney, Agent, or Firm* — Taylor English Duma LLP

(57) ABSTRACT

Example aspects of a deployment probe for deploying a stent, a pipe repair assembly, and a method for repairing a pipeline are disclosed. The deployment probe for deploying a stent can comprise a probe body defining an inner surface, an outer surface, and a slot extending from the inner surface to the outer surface, the inner surface defining a probe void, the probe void defining a probe axis, the slot extending in an axial direction relative to the probe axis; and a release mechanism comprising a retainer body received within the probe void and a stent retainer coupled to the retainer body, the stent retainer substantially aligned with the slot and configured to engage a stent.

12 Claims, 11 Drawing Sheets

(56) References Cited

U.S. PATENT DOCUMENTS

| | | | |
|---|---|---|---|
| 7,172,370 | B2 | 2/2007 | Schmidt |
| 7,267,141 | B1 | 9/2007 | De Meyer et al. |
| 8,488,290 | B2 | 7/2013 | Kauffman |
| 8,783,297 | B2 | 7/2014 | Hawwa et al. |
| 9,052,051 | B2 | 6/2015 | Maimets et al. |
| 10,641,427 | B2 | 5/2020 | Braun et al. |
| 11,079,058 | B2 | 8/2021 | Furcoiu |
| 11,187,366 | B2 | 11/2021 | Furcoiu |
| 11,221,099 | B2 | 1/2022 | Braun et al. |
| 2002/0144822 | A1 | 10/2002 | Hackworth et al. |
| 2003/0017775 | A1 | 1/2003 | Sowinski et al. |
| 2003/0233140 | A1* | 12/2003 | Hartley .............. A61M 25/00 623/1.11 |
| 2004/0236398 | A1 | 11/2004 | Burgmeier et al. |
| 2008/0140178 | A1 | 6/2008 | Rasmussen et al. |
| 2008/0255660 | A1 | 10/2008 | Guyenot et al. |
| 2008/0269789 | A1 | 10/2008 | Eli |
| 2010/0010617 | A1* | 1/2010 | Goodson, IV .......... A61F 2/966 623/1.11 |
| 2010/0049313 | A1* | 2/2010 | Alon .................. A61F 2/2439 623/2.11 |
| 2010/0263759 | A1 | 10/2010 | Maimets et al. |
| 2011/0264186 | A1 | 10/2011 | Berglung et al. |
| 2012/0273078 | A1 | 11/2012 | Hawwa et al. |
| 2013/0018450 | A1 | 1/2013 | Hunt |
| 2013/0131783 | A1 | 5/2013 | Shalev et al. |
| 2013/0158646 | A1 | 6/2013 | Roeder |
| 2016/0120638 | A1 | 5/2016 | Michalak |
| 2016/0143732 | A1 | 5/2016 | Glimsdale |
| 2016/0238178 | A1 | 8/2016 | Urbanski |
| 2017/0231765 | A1* | 8/2017 | Desrosiers ............ A61F 2/2418 623/2.11 |
| 2017/0304092 | A1 | 10/2017 | Hong et al. |
| 2019/0093813 | A1 | 3/2019 | Badger et al. |
| 2019/0301657 | A1 | 10/2019 | Braun et al. |
| 2020/0224811 | A1 | 7/2020 | Braun et al. |
| 2020/0263823 | A1 | 8/2020 | Furcoiu |
| 2020/0292119 | A1 | 9/2020 | Furcoiu |
| 2020/0292120 | A1 | 9/2020 | Furcoiu |
| 2021/0041051 | A1 | 2/2021 | Furcoiu |
| 2021/0041052 | A1 | 2/2021 | Furcoiu |
| 2021/0381637 | A1 | 12/2021 | Furcoiu |

FOREIGN PATENT DOCUMENTS

| | | |
|---|---|---|
| KR | 1020070018627 | 2/2007 |
| WO | 2011001189 | 1/2011 |
| WO | 2019194870 | 10/2019 |
| WO | 2020172136 | 8/2020 |
| WO | 2020219294 | 10/2020 |

OTHER PUBLICATIONS

US 11,131,417 B2, 09/2021, Braun et al. (withdrawn)

Braun, Clifton; Non-Final Office Action for U.S. Appl. No. 16/112,207, filed Aug. 24, 2018, dated Nov. 5, 2019, 14 pgs.

Braun, Clifton; Notice of Allowance for U.S. Appl. No. 16/112,207, filed Aug. 24, 2018, dated Feb. 13, 2020, 13 pgs.

Braun, Clifton; International Search Report for PCT Application No. PCT/US18/63325, filed Nov. 30, 2018, dated Feb. 5, 2019, 8 pgs.

Furcoiu, Aurelian Ioan; International Search Report and Written Opinion for PCT Application No. PCT/US20/18593, filed Feb. 18, 2020, dated May 7, 2020, 9 pgs.

Braun, Clifton; International Preliminary Report on Patentability for PCT Application No. PCT/US18/63325, filed Nov. 30, 2018, dated Oct. 15, 2020, 7 pgs.

Furcoiu, Aurelian Ioan; International Search Report and Written Opinion for PCT Application No. PCT/US20/28038, filed Apr. 14, 2020, dated Jun. 24, 2020, 9 pgs.

Braun, Clifton; Non-Final Office Action for U.S. Appl. No. 16/836,468, filed Mar. 31, 2020, dated May 20, 2021, 29 pgs.

Furcoiu, Aurelian Ioan; Non-Final Office Action for U.S. Appl. No. 16/792,984, filed Feb. 18, 2020, dated May 25, 2021, 25 pgs.

Furcoiu, Aurelian Ioan; Corrected Notice of Allowance for U.S. Appl. No. 16/786,193, filed Feb. 10, 2020, dated May 17, 2021, 6 pgs.

Furcoiu, Aurelian Ioan; Corrected Notice of Allowance for U.S. Appl. No. 16/786,193, filed Feb. 10, 2020, dated Jun. 22, 2021, 6 pgs.

Furcoiu, Aurelian Ioan; Notice of Allowance for U.S. Appl. No. 16/786,193, filed Feb. 10, 2020, dated Apr. 26, 2021, 9 pgs.

Furcoiu, Aurelian Ioan; Requirement for Restriction/Election for U.S. Appl. No. 17/792,984, filed Feb. 18, 2020, dated Apr. 1, 2021, 6 pgs.

Furcoiu, Aurelian Ioan; Non-Final Office Action for U.S. Appl. No. 16/786,193, filed Feb. 10, 2020, dated Feb. 4, 2021, 22 pgs.

Furcoiu, Aurelian Ioan; Non-Final Office Action for U.S. Appl. No. 16/786,246, filed Feb. 10, 2020, dated Mar. 4, 2021, 21 pgs.

Furcoiu, Aurelian Ioan; Requirement for Restriction/Election for U.S. Appl. No. 16/786,246, filed Feb. 10, 2020, dated Feb. 3, 2021, 6 pgs.

Braun, Clifton; Notice of Allowance for U.S. Appl. No. 16/836,468, filed Mar. 31, 2020, dated Oct. 1, 2021, 9 pgs.

Furcoiu, Aurelian Ioan; Final Office Action for U.S. Appl. No. 16/792,984, filed Feb. 18, 2020, dated Nov. 24, 2021, 15 pgs.

Furcoiu, Aurelian Ioan; Notice of Allowance for U.S. Appl. No. 16/786,246, filed Feb. 10, 2020, dated Oct. 14, 2021, 9 pgs.

Furcoiu, Aurelian Ioan; International Preliminary Report on Patentability for PCT Application No. PCT/US20/28038, filed Apr. 14, 2020, dated Nov. 4, 2021, 8 pgs.

Furcoiu, Aurelian Ioan; Non-Final Office Action for U.S. Appl. No. 16/987,067, filed Aug. 6, 2020, dated Dec. 7, 2021, 32 pgs.

Braun, Clifton; Corrected Notice of Allowance for U.S. Appl. No. 16/836,468, filed Mar. 31, 2020, dated Aug. 31, 2021, 6 pgs.

Braun, Clifton; Notice of Allowance for U.S. Appl. No. 16/836,468, filed Mar. 31, 2020, dated Aug. 12, 2021, 13 pgs.

Furcoiu, Aurelian Ioan; Corrected Notice of Allowance for U.S. Appl. No. 16/786,246, filed Feb. 10, 2020, dated Aug. 31, 2021, 6 pgs.

Furcoiu, Aurelian Ioan; Corrected Notice of Allowance for U.S. Appl. No. 16/786,246, filed Feb. 10, 2020, dated Aug. 6, 2021, 7 pgs.

Braun, Cliff; Extended European Search report for application No. 18913510.6, filed Nov. 30, 2018, dated Sep. 13, 2021, 7 pgs.

Furcoiu, Aurelian Ioan; International Preliminary Report on Patentability for PCT Application No. PCT/US20/18593, filed Feb. 18, 2020, dated Sep. 2, 2021, 8 pgs.

Furcoiu, Aurelian Ioan; Notice of Allowance for U.S. Appl. No. 16/792,984, filed Feb. 28, 2020, dated Jan. 31, 2022, 9 pgs.

Furcoiu, Aurelian Ioan; Notice of Allowance for U.S. Appl. No. 16/987,067, filed Aug. 6, 2020, dated Jan. 5, 2022, 13 pgs.

* cited by examiner

PIPE REPAIR ASSEMBLY

CROSS-REFERENCE TO RELATED APPLICATIONS

The present application claims the benefit of U.S. Provisional Application No. 62/838,073, filed Apr. 24, 2019, which is hereby specifically incorporated by reference herein in its entirety.

TECHNICAL FIELD

This disclosure relates to pipe repair. More specifically, this disclosure relates to a pipe repair assembly comprising a stent and a deployment probe for deploying the stent.

BACKGROUND

Piping systems, including municipal water systems, can develop breaks in pipe walls that can cause leaking. Examples of breaks in a pipe wall can include radial cracks, axial cracks, point cracks, etc. Repairing a break in a pipe wall often requires the piping system to be shut off, which can be inconvenient for customers and costly for providers. Further, repairs can necessitate grandiose construction, including the digging up of streets, sidewalks, and the like, which can be costly and time-consuming.

SUMMARY

It is to be understood that this summary is not an extensive overview of the disclosure. This summary is exemplary and not restrictive, and it is intended neither to identify key or critical elements of the disclosure nor delineate the scope thereof. The sole purpose of this summary is to explain and exemplify certain concepts off the disclosure as an introduction to the following complete and extensive detailed description.

Disclosed is a deployment probe for deploying a stent, the deployment probe comprising a probe body defining an inner surface, an outer surface, and a slot extending from the inner surface to the outer surface, the inner surface defining a probe void, the probe void defining a probe axis, the slot extending in an axial direction relative to the probe axis; and a release mechanism comprising a retainer body received within the probe void and a stent retainer coupled to the retainer body, the stent retainer substantially aligned with the slot and configured to engage a stent.

Also disclosed is a pipe repair assembly comprising a stent moveable between a compressed configuration and an expanded configuration; and a deployment probe comprising a release mechanism, the release mechanism moveable between an engaged position, wherein the release mechanism is engaged with the stent and the stent is in the compressed configuration, and a disengaged position, wherein the release mechanism is disengaged from the stent and the stent is in the expanded configuration.

A method for repairing a pipeline is also disclosed, the method comprising providing a stent comprising a seal and a stent spring, the stent spring comprising an engagement tab; engaging the engagement tab with a release mechanism of a deployment probe to orient the stent in a compressed configuration, wherein the deployment probe and stent together define a pipe repair assembly; navigating the pipe repair assembly through a pipeline to a crack in the pipeline; disengaging the engagement tab from the release mechanism; and biasing the stent to an expanded configuration in the pipeline.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures may be designated by matching reference characters for the sake of consistency and clarity.

DETAILED DESCRIPTION

Figure 1:
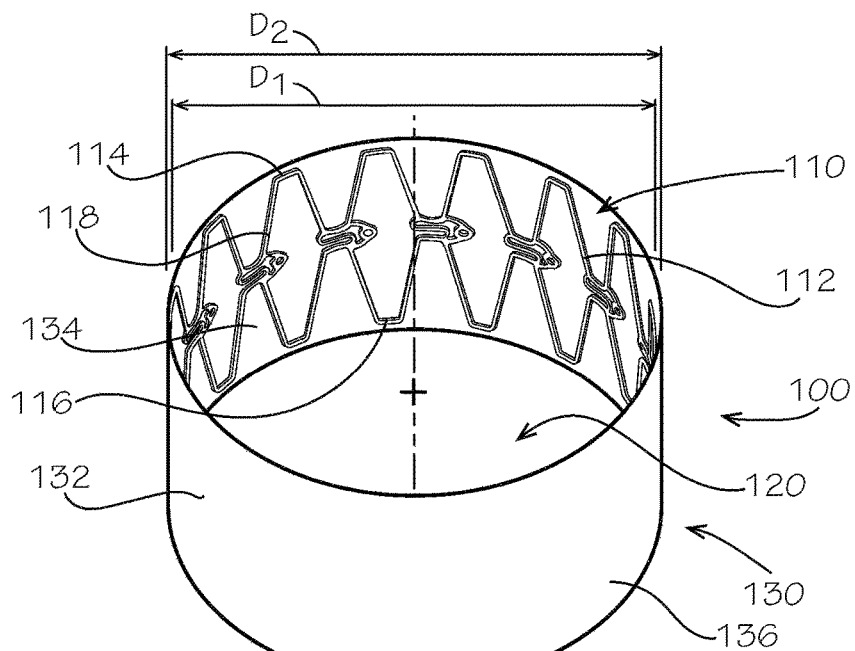
FIG. 1 is a top perspective view of a stent, in accordance with one aspect of the present disclosure.

The present disclosure can be understood more readily by reference to the following detailed description, examples, drawings, and claims, and the previous and following description. However, before the present devices, systems, and/or methods are disclosed and described, it is to be understood that this disclosure is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description is provided as an enabling teaching of the present devices, systems, and/or methods in its best, currently known aspect. To this end, those skilled in the relevant art will recognize and appreciate that many changes can be made to the various aspects of the present devices, systems, and/or methods described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

As used throughout, the singular forms "a," "an" and "the" include plural referents unless the context clearly dictates otherwise. Thus, for example, reference to "an element" can include two or more such elements unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

For purposes of the current disclosure, a material property or dimension measuring about X or substantially X on a particular measurement scale measures within a range between X plus an industry-standard upper tolerance for the specified measurement and X minus an industry-standard lower tolerance for the specified measurement. Because tolerances can vary between different materials, processes and between different models, the tolerance for a particular measurement of a particular component can fall within a range of tolerances.

As used herein, the terms "optional" or "optionally" mean that the subsequently described event or circumstance can or cannot occur, and that the description includes instances where said event or circumstance occurs and instances where it does not.

The word "or" as used herein means any one member of a particular list and also includes any combination of members of that list. Further, one should note that conditional language, such as, among others, "can," "could," "might," or "may," unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily include logic for deciding, with or without user input or prompting, whether these features, elements and/or steps are included or are to be performed in any particular aspect.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutations of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific aspect or combination of aspects of the disclosed methods.

Disclosed in the present application is a pipe repair assembly and associated methods, systems, devices, and various apparatus. Example aspects of the pipe repair assembly can comprise a stent and a deployment probe for deploying the stent within a pipe. It would be understood by one of skill in the art that the disclosed pipe repair assembly is described in but a few exemplary aspects among many. No particular terminology or description should be considered limiting on the disclosure or the scope of any claims issuing therefrom.

Figure 2:
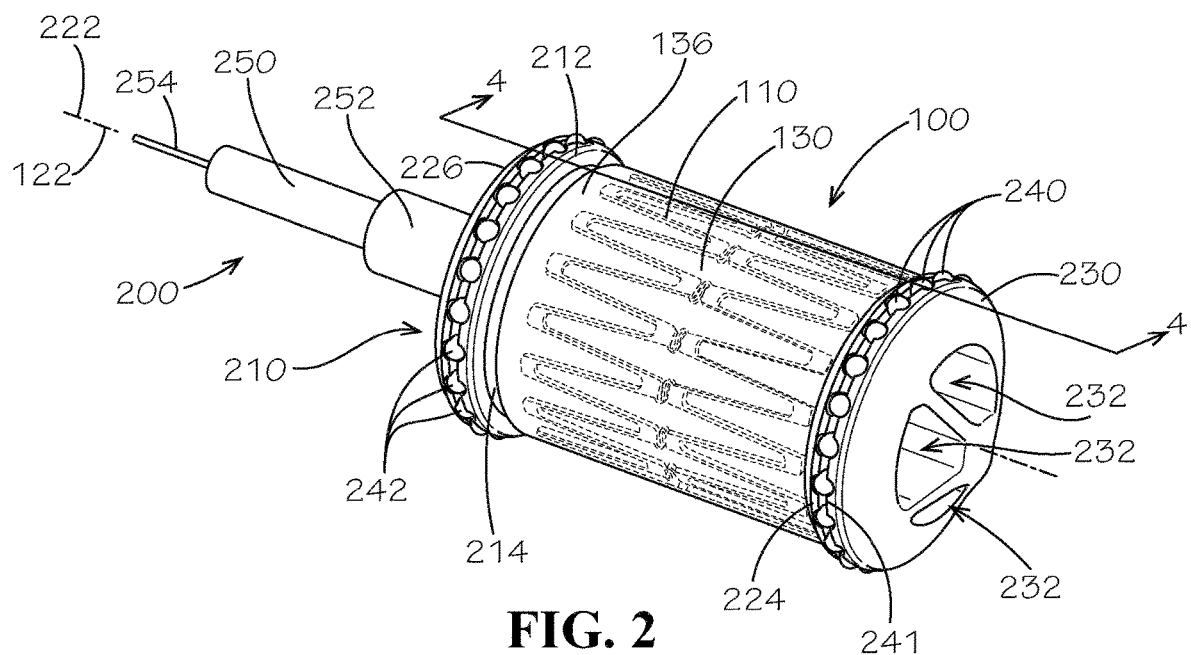
FIG. 2 is a top perspective view of a pipe repair assembly, in accordance with one aspect of the present disclosure, wherein the pipe repair assembly comprises a deployment probe and the stent of FIG. 1.

FIG. 1 illustrates a first aspect of a stent 100, according to the present disclosure. Example aspects of the stent 100 can comprise a stent spring 110 and a seal 130. Example aspects of the stent spring 110 can define a spring force and can be expandable and compressible, such that the stent 100 can be oriented in a natural, expanded configuration, as shown in FIG. 1, and a compressed configuration, as shown in FIG. 2. The stent 100 can also define an overall stent diameter Dz. According to example aspects, the stent 100 can be expanded within a pipe 370 (shown in FIG. 3) such that the seal 130 can engage an inner wall 372 (shown in FIG. 3) of the pipe 370 where a crack 374 (shown in FIG. 3) or other damage is present in order to create a watertight seal between the stent 100 and the inner wall 372 of the pipe 370 to prevent leaking at the damage site.

As shown in FIG. 1, the stent spring 110 can bias the stent 100 to the expanded configuration. In the depicted aspect, the stent spring 110 can be formed as a substantially tubular mesh structure 112 defining opposing open ends (e.g. a top end 114 and a bottom end 116). The stent spring 110 can further define an outer surface (not shown) and an opposite inner surface 118. The inner surface 118 can generally define a stent void 120 through a center of the stent spring 110. The stent void 120 can extend between the open top and bottom ends 114,116 of the stent spring 110 and can allow fluid to pass therethrough. A stent axis 122 can extend substantially through a center of the stent void 120, as shown. Example aspects of the stent spring 110 can also define a stent spring diameter $D_1$.

In some aspects, the stent spring 110 can comprise a metal material, such as, for example, stainless steel, spring steel, aluminum, nitinol, or cobalt chromium. In other aspects, the stent spring 110 can comprise a plastic material, such as, for example, nylon, POM (polyoxymethylene), or PVC (polyvinyl chloride), and in still other aspects, the stent spring 110 can comprise a carbon fiber material. Other aspects of the stent spring 110 can comprise any other suitable material known in the art. Optionally, the material of the stent spring 110 can be an NSF certified material that can comply with various public health safety standards. For example, in some aspects, the material can be approved as safe for use in drinking-water applications. Moreover, in some aspects, the stent spring 110 can comprise a coating, such as, for example, a rubber or liquid metal coating. The coating can improve mechanical properties of the stent spring 110. For example, the coating can improve the tensile strength of the stent spring 110 by providing a flexible and/or springy outer layer. In some aspects, the coating can also be corrosion resistant, or a separate coating can be applied for corrosion resistance. For example, a corrosion resistant coating can comprise a zinc-nickel material, phosphate, electrophoretic paint (e-coating), polyester, fusion-bonded epoxy (FBE), or any other suitable corrosion resistant material.

According to example aspects, the seal 130 can be formed as a hollow tubular sleeve 132 configured to receive the stent spring 110 therein. The seal 130 can define an inner surface 134 and an outer surface 136, as shown. Example aspects of the seal 130 can comprise a flexible and stretchable material, such as, for example, neoprene. In other aspects, the seal 130 can be formed from another synthetic rubber material such as EPDM rubber, or can be formed from natural rubber, foam, epoxy, silicone, a resin-soaked cloth, or any other suitable flexible material for providing a watertight seal. In the present aspect, the seal 130 can be retained on the stent spring 110 by snugly wrapping around the stent spring 110 to create a friction fit between the seal 130 and the stent spring 110. According to other example aspects, the seal 130 can be retained on the stent spring 110 by stitching, adhesives, ties, clips, or any other suitable fastener or combination of fasteners known in the art. According to example aspects, when the seal 130 is assembled with the stent spring 110, the inner surface 134 of the seal 130 can engage the outer surface (not shown) of the stent spring 110.

FIG. 2 illustrates a first aspect of a pipe repair assembly 200, according to the present disclosure. Example aspects of the pipe repair assembly 200 can be sized and shaped to be easily inserted into and navigable through the pipe 370 (shown in FIG. 3) or pipeline to a location of the crack 374 (shown in FIG. 3) or other damage. The pipe repair assembly 200 can comprise the stent 100 and a deployment probe 210 for deploying the stent 100 within the damaged pipe 370. Example aspects of the deployment probe 210 can comprise a substantially cylindrical probe body 212, as shown. The stent 100 of the present aspect can be configured to wrap around a circumference of the probe body 212 and to engage an outer surface 214 thereof, as shown. An inner surface 315 (shown in FIG. 3) of the probe body 212 can define an interior probe void 310 (shown in FIG. 3), and a probe axis 222 can extend through a center of the probe void 310. Example aspects of the probe axis 222 and stent axis 122 can be substantially co-linear when the stent 100 is mounted on the deployment probe 210. The probe body 212 can also define a front end 224 and a rear end 226. As shown, a probe head 230 can be connected to or monolithically formed with the probe body 212 at the front end 224. Example aspects of the probe head 230 can define one or more front openings 232 formed therethrough, wherein the front openings 232 can be in fluid communication with the probe void 310. The probe body 212 can also define one or more rear openings 342 (shown in FIG. 3) formed at the rear end 226, such that fluid in the pipe 370 can flow through the front openings 232, into the probe void 310, and out of the rear openings 342, or in the opposite direction. As such, fluid in the pipe 370 can continue to flow substantially uninterrupted as the pipe repair assembly 200 is navigated through the pipe 370 or pipeline. In some aspects, the deployment probe 210 can comprise front ball bearings 240 positioned around an outer circumference 241 of the probe head 230, as shown, and/or at the front end 224 of the probe body 212. In the present aspect, rear ball bearings 242 are also positioned around the outer circumference of the probe body 212 at the rear end 226. The front and rear ball bearings 240,242 can facilitate the navigation of the deployment probe 210 through the pipe 370 and/or a pipeline.

Example aspects of the deployment probe 210 can comprise a navigation stem 250 extending from the rear end 226 of the probe body 212. The navigation stem 250 can aid in driving and steering the pipe repair assembly 200 through the pipe 370 or pipeline. In example aspects, the navigation stem 250 can be formed from plastic, while in other aspects, the navigation stem 250 can be formed from another suitable resilient material, such as a rubber material. In some aspects, a flexible damper 252 can surround the navigation stem 250 at the joint between the navigation stem 250 and the probe body 212 to allow for improved flexibility of the navigation stem 250 as it bends during navigation through a non-linear pipe or pipeline. For example, in some aspects, the damper 252 can be formed from a rubber material or any other suitably flexible material. Example aspects of the deployment probe 210 can also comprise a release cable 254 extending within the navigation stem 250, as illustrated. Example aspects of the release cable 254 can be formed from a metal material, such as, for example, steel. Other aspects of the release cable 254 can be formed from another suitable material, such, for example, a plastic material.

Figure 3:
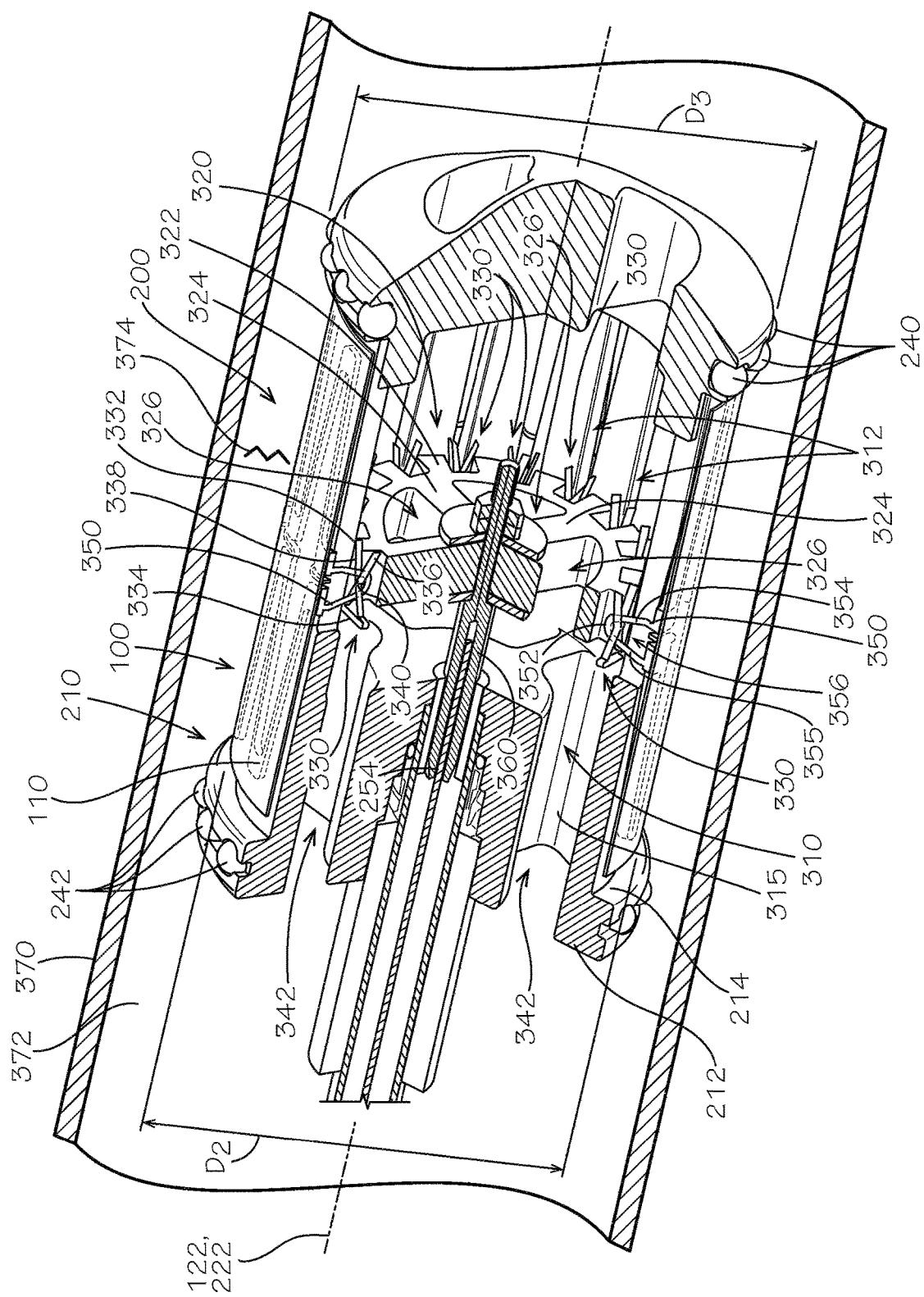
FIG. 3 is a cut-away view of the pipe repair assembly of FIG. 2, wherein a release mechanism of the pipe repair assembly is in an engaged position.

FIG. 3 illustrates a cutaway view of the pipe repair assembly 200, such that the probe void 310 of the deployment probe 210 is visible. As shown, the deployment probe 210 can define a plurality of slots 312 formed in the probe body 212 and extending in the axial direction relative to the probe axis 222. Each of the slots 312 can extend from the outer surface 214 of the cylindrical probe body 212 to the inner surface 315 of the cylindrical probe body 212. Furthermore, the stent spring 110 of the stent 100 can comprise one or more engagement tabs 350 extending radially inward relative to the probe axis 222. Each engagement tab 350 can be received through a corresponding one of the slots 312, such that a distal portion 352 of each engagement tab 350 can extend into the probe void 310 of the deployment probe 210. In the present aspect, each of the engagement tabs 350 can generally comprise a looped structure 354 defining a tab opening 356 therethrough.

Example aspects of the deployment probe 210 can comprise a release mechanism 320 positioned within the probe void 310 defined by the probe body 212, as shown. According to example aspects, the release mechanism 320 can comprise a retainer body, such as a retainer wheel 322, and a plurality of stent retainers, such as retainer clips 330. The retainer clips 330 can be mounted to the retainer wheel 322. The retainer wheel 322 can comprise a plurality of spokes 324, which can define retainer wheel openings 326 therebetween to allow for the flow of fluid therethrough. The retainer wheel 322 can be operatively connected to the release cable 254, and the release cable 254 can be operated (for example, by a remote operator) to move the retainer wheel 322 axially within the probe void 310. In some aspects, a crimped, threaded connector 360 can be attached to the release cable 254 and can be threadably connected to the retainer wheel 322. The retainer clips 330 can be mounted to the retainer wheel 322 such that axial movement of the retainer wheel 322 can result in axial movement of the retainer clips 330. Example aspects of the release mechanism 320 can be movable by the release cable 254 between an engaged position, as shown, wherein each retainer clip 330 can releasably engage a corresponding one of the engagement tabs 350 of the stent 100, and a disengaged position (shown in FIG. 5), wherein each retainer clip 330 can be disengaged from the corresponding engagement tab 350. In the engaged position, the stent 100 can be retained in the compressed configuration, as shown, and in the disengaged position, the stent 100 can be allowed to move to the expanded configuration.

As shown, in the present aspect, each of the retainer clips 330 can substantially define an X-shape and can define a first end 332 and a second end 334. Each retainer clip 330 can comprise a first spring leg 336 and a second spring leg 338 bent towards one another in a generally V-shape to define a pinched middle section 340, as shown. In some aspects, a narrow clip passage (not shown) can be defined at the pinched middle section 340 between the corresponding first spring leg 336 and second spring leg 338. In other aspects, the first spring leg 336 and second spring leg 338 can be touching at the pinched middle section 340 but can be pushed apart by a force to define the clip passage. Example aspects of the clip passages can each define a width that can be less than a width of the looped structure 354 of the corresponding engagement tab 350 when the corresponding first and second spring legs 336,338 are in their natural, unbiased orientation. To engage each retainer clip 330 with the corresponding engagement tab 350, the engagement tab 350 be positioned between the first and second spring legs 336,338 at the first end 332 of the retainer clip 330 and can be slid axially towards the pinched middle section 340. A first side 355 of the looped structure 354 of the engagement tab 350 can be pushed through the narrow clip passage, biasing the first and second spring legs 336,338 outward. When the first side 355 of the looped structure 354 has passed through the clip passage, the first and second spring legs 336,338 can be naturally biased back towards one another, and the pinched middle section 340 of the retainer clip 330 can be received within the tab opening 356. The engagement tab 350 can be prevented from disengaging the retainer clip 330 by the positioning of the pinched middle section 340 within the tab opening 356, until a sufficient force is applied to bias the first and second spring legs 336,338 apart and push the looped structure 354 back through the clip passage of the retainer clip 330.

With the release mechanism 320 in the engaged position and the retainer clips 330 engaged with the corresponding engagement tabs 350, the stent 100 can be pulled radially inward relative to the stent axis 122 to the compressed configuration. In the compressed configuration, the diameter $D_1$ (shown in FIG. 1) of the stent spring 110 can be reduced. The reduced diameter $D_1$ of the stent spring 110 can result in a reduced overall stent diameter $D_2$ of the stent 100, along with a reduced overall stent volume of the stent 100. The reduced overall stent diameter $D_2$ can allow for easier insertion and navigation of the pipe repair assembly 200 into and through the pipe 370 (shown in FIG. 3) or pipeline. The size and shape of the deployment probe 210 and the front and rear ball bearings 240,242 can also facilitate the insertion and navigation of the pipe repair assembly 200 through the pipe 370. In the present aspect, the overall stent diameter $D_2$ in the compressed configuration can be less than a maximum diameter $D_3$ of the deployment probe 210, as shown. In other aspects, the overall stent diameter $D_2$ can be about equal to or greater than the maximum diameter $D_3$ of the deployment probe 210.

Figure 4:
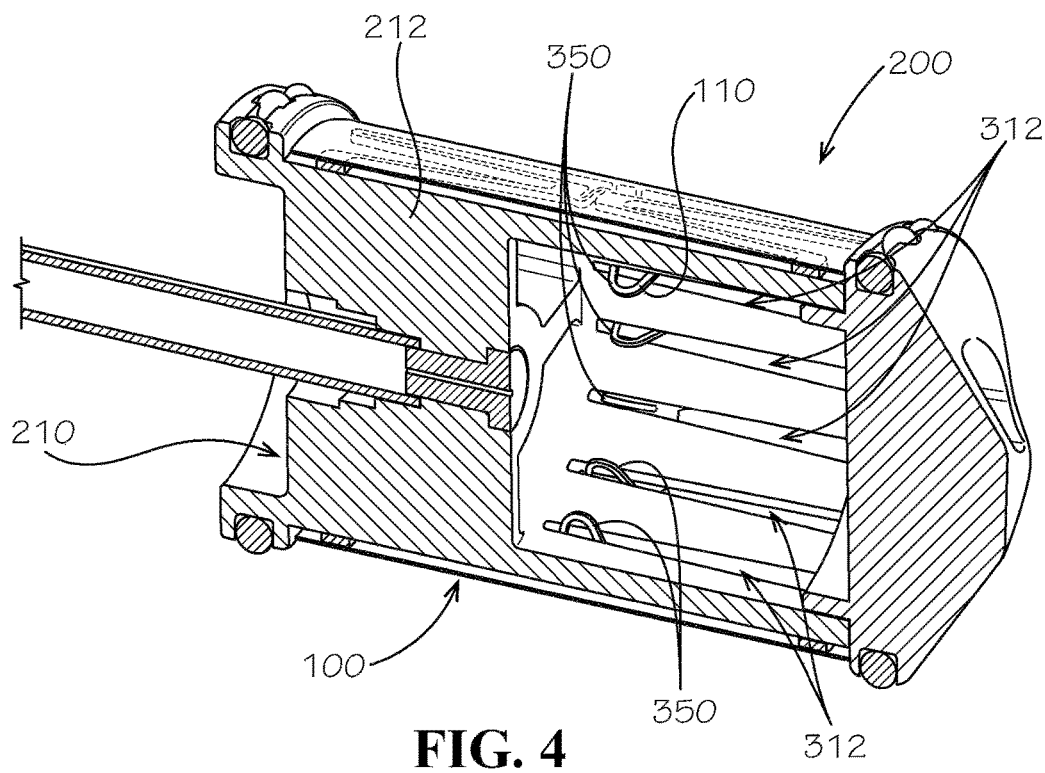
FIG. 4 is a cross-sectional view of the pipe repair assembly of FIG. 2 taken along line 4-4 of FIG. 2, wherein the release mechanism of FIG. 3 is removed for visibility of engagement tabs of the stent of FIG. 1.

FIG. 4 illustrates pipe repair assembly 200 with the release mechanism 320 (shown in FIG. 3) removed, such that the engagement tabs 350 of the stent spring 110 can be clearly viewed extending through the corresponding slots 312 in the probe body 212.

Figure 5:
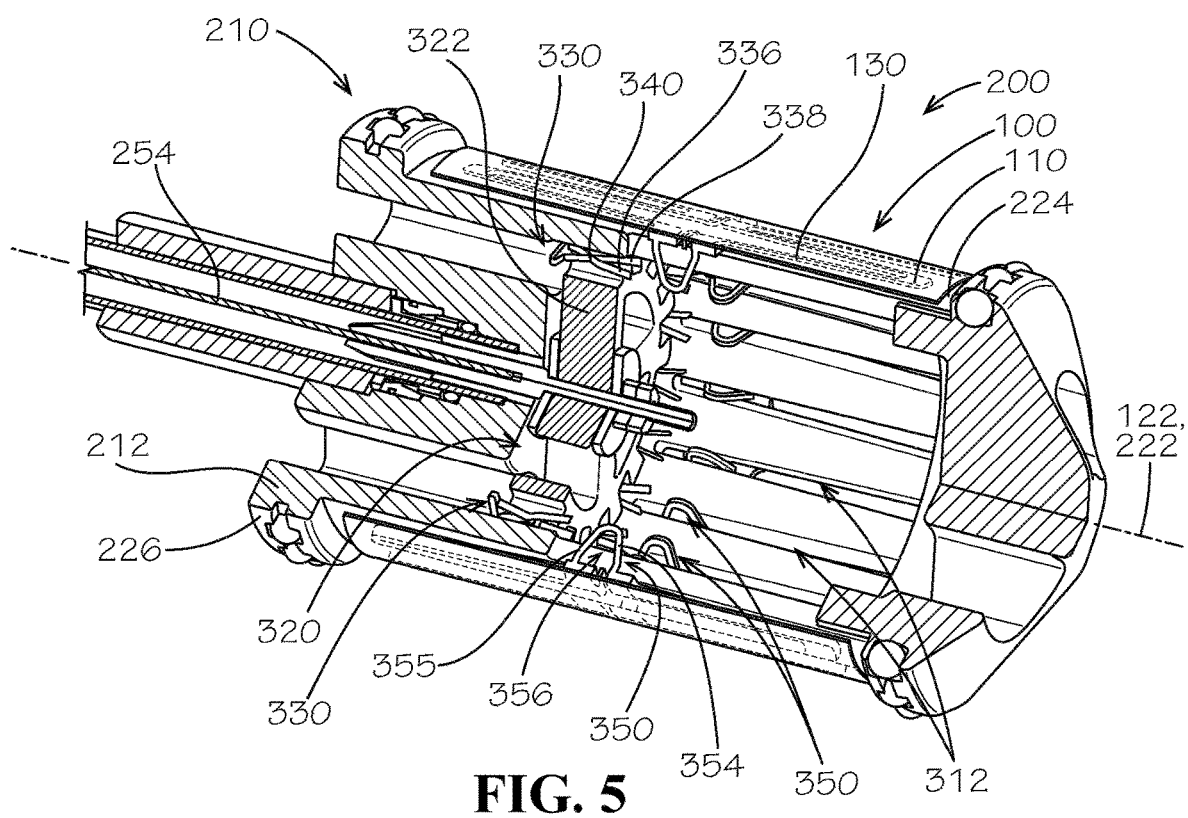
FIG. 5 is a cut-away view of the pipe repair assembly of FIG. 2, wherein the release mechanism of FIG. 3 is in a disengaged position.

Referring to FIG. 5, to move the release mechanism 320 from the engaged position to the disengaged position, the release cable 254 can be operated (for example, by the remote operator) to move the retainer wheel 322 axially towards the rear end 226 of the probe body 212, thus axially moving the retainer clips 330 towards the rear end 226 of the probe body 212. As the retainer clips 330 move towards the rear end 226, the pinched middle section 340 of each retainer clip 330 can be pushed against the first side 355 of the looped structure 354 of the corresponding engagement tab 350, which can bias the first and second spring legs 336,338 apart and allow the first side 355 of the looped structure 354 to pass through the clip passage. Once the retainer clips 330 are disengaged from the engagement tabs 350 of the stent spring 110, the spring force of the stent spring 110 can bias the stent 100 radially outward to the expanded configuration. The diameter $D_1$ (shown in FIG. 1) of the stent spring 110 can increase as the stent 100 expands, disengaging the engagement tabs 350 from the slots 312 of the probe body 212. As the diameter $D_1$ of the stent spring 110 increases, the stent spring 110 can bias the seal 130 radially outward into engagement with the inner wall 372 (shown in FIG. 3) of the pipe 370 (shown in FIG. 3). With the stent 100 expanded and disengaged from the deployment probe 210, the deployment probe 210 can be removed from the pipe 370 or pipeline, and fluid can flow freely through the expanded stent 100. In other aspects, the retainer wheel 322 may be moved axially towards the front end 224 of the probe body 212 to disengage the retainer clips 330 from the engagement tabs 350.

In use, the pipe repair assembly 200 can be inserted into the pipe 370 or pipeline and the stent 100 can be aligned with the crack 374 (shown in FIG. 3) or other damage. One aligned, the stent 100 can be expanded within the pipe 370, such that the seal 130 can engage the inner wall 372 of the pipe 370 where the crack 374 is present, in order to create a watertight seal between the stent 100 and the inner wall 372 to prevent leaking at the damage site. The stent 100 can be expanded by moving the release mechanism 320 towards the rear end 226 (or front end 224 in some aspects) of the probe body 212 from the engaged position to the disengaged position. Each retainer clip 330 can disengage the corresponding engagement tab 350 of the stent spring 110 as the release mechanism 320 moves towards the disengaged position. The spring force of the stent spring 110 can then bias the stent 100 to the expanded configuration, increasing diameter $D_1$ (shown in FIG. 1) of the stent spring 110 and the overall stent diameter $D_2$ (shown in FIG. 1). The stent spring 110 can define its largest diameter in the expanded configuration. The increased diameter $D_1$ of the stent spring 110 can bias the seal 130 radially outward relative to the stent axis 122, such that the seal 130 can move towards and press against the inner wall 372 of the pipe 370. In some aspects, in the fully expanded configuration, the overall stent diameter $D_2$ can be slightly greater than a diameter of the inner wall 372 of the pipe 370, such that the stent 100 can apply a force in the radial direction, relative to the stent axis 122, against the inner wall 372 of the pipe 370.

As such, a method for repairing the pipe 370 can comprise engaging the engagement tabs 350 of the stent 100 with the corresponding retainer clips 330 of the release mechanism 320 in order to orient the stent 100 in the compressed configuration. The method can further comprise inserting the pipe repair assembly 200 into the pipe 370 and orienting the pipe repair assembly 200 proximate to a crack 374 or other damage in the pipe 370. The method can then comprise disengaging the engagement tabs 350 from the retainer clips 330 to allow the spring force of the stent spring 110 to bias the stent 100 to the expanded configuration. Example aspects of the method can also comprise engaging the inner wall 372 of the pipe 370 at the crack 374 (or other damage) with the seal 130 of the stent 100 to create a watertight seal between the stent 100 and the inner wall 372 of the pipe 370.

Figure 6:
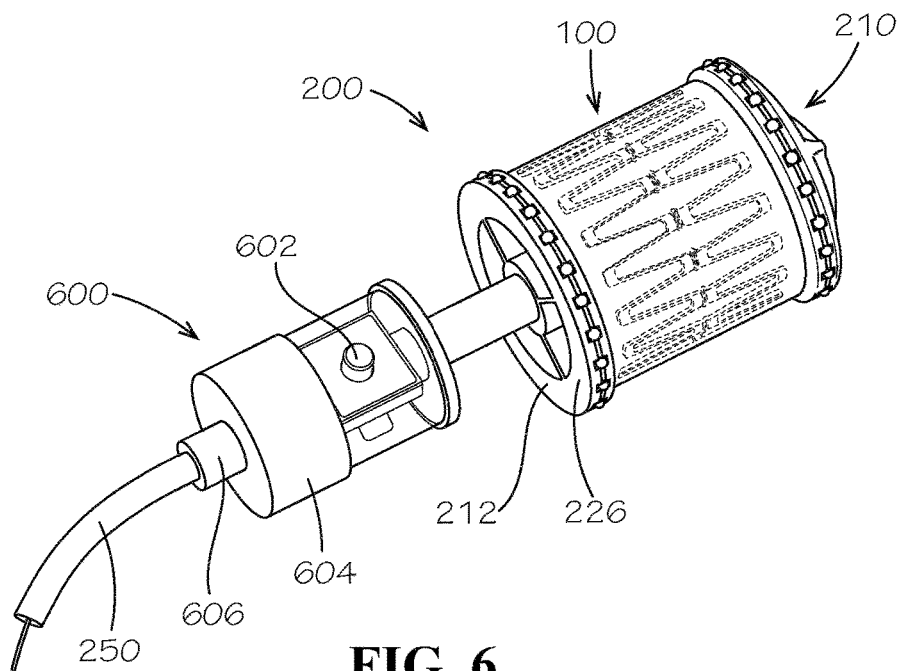
FIG. 6 is a top perspective view of the pipe repair assembly of FIG. 2 further comprising a damage detection system.

FIG. 6 illustrates another example aspect of the pipe repair assembly 200 further comprising a damage detection system 600 attached thereto. In the present aspect, the damage detection system 600 can be coupled to the navigation stem 250 proximate to the rear end 226 of the probe body 212. Other aspects of the damage detection system 600 can be attached elsewhere to the pipe repair assembly 200. The damage detection system 600 can comprise an image sensor, such as a camera 602, for visually identifying the damaged region of the pipe 370 (shown in FIG. 3). In some aspects, the damage detection system 600 can stream video or photographic data collected via the camera 602 to a remote operator in order to manually identify the damaged region based on the visibility of damage to the pipe 370. As shown, the camera 602 or other image sensor can be disposed within a protective housing 604. In some aspects, a second flexible damper 606 can surround the navigation stem 250 at the joint between the navigation stem 250 and the protective housing 604 to allow for improved flexibility of the navigation stem 250 as it bends during navigation through a non-linear pipe or pipeline.

Figure 7:
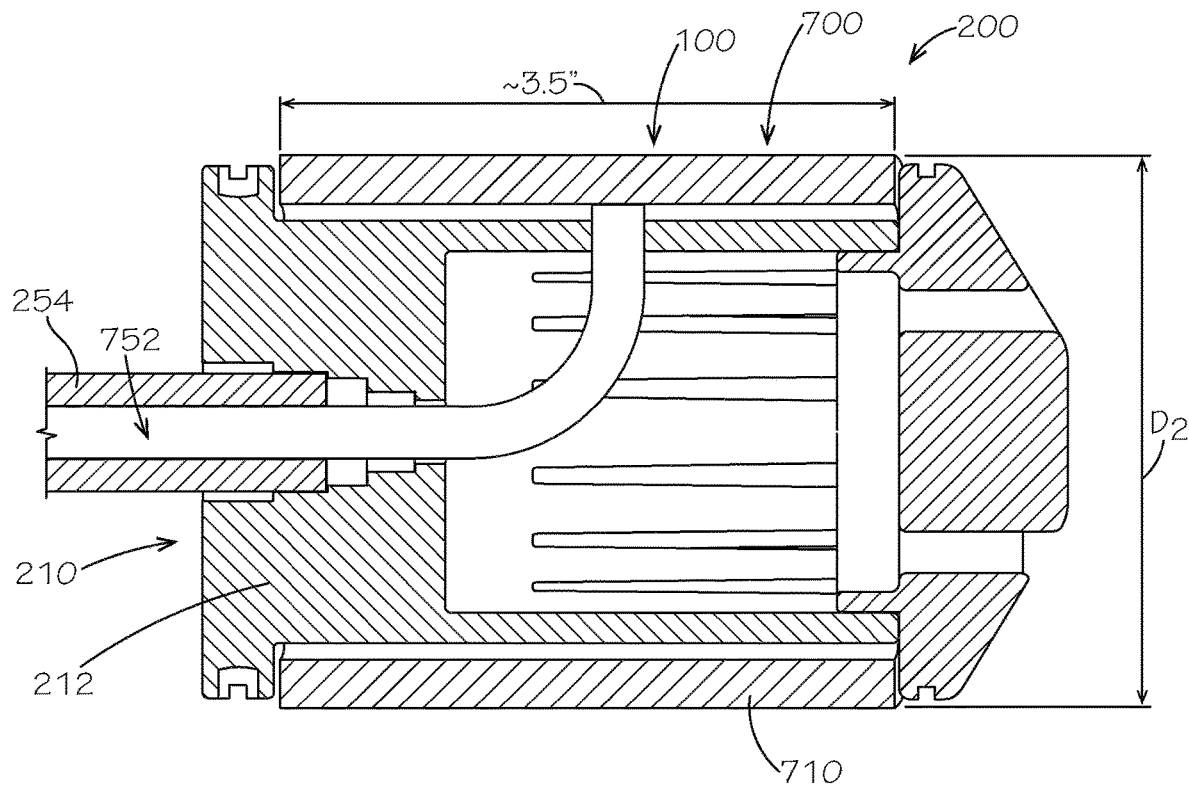
FIG. 7 is a cross-sectional view of the pipe repair assembly according to another aspect of the present disclosure.

FIG. 7 illustrates a cross-sectional view of another aspect of the pipe repair assembly 200, wherein the stent 100 can be an inflatable stent 700. In some aspects, the inflatable stent 700 can comprise a rigid support cylinder (not shown) encompassed by a substantially cylindrical bladder 710. However, in the present aspect, the inflatable stent 700 comprises the bladder 710 only. Example aspects of the bladder 710 can comprise a flexible and stretchable material, such as, for example, silicone. In other aspects, the bladder 710 can be formed from neoprene, EPDM rubber, natural rubber, foam, epoxy, or any other suitable flexible material for providing a watertight seal. The bladder 710 can configurable in an inflated configuration and a deflated configuration (shown in the present FIG. 7). The bladder 710 can be mounted to the probe body 212 of the deployment probe 210 in the deflated configuration, and can be inserted into the pipe 370 (shown in FIG. 3) or pipeline and navigated to the location of the crack 374 (shown in FIG. 3) or other damage. Once aligned with the crack 374 or other damage, the bladder 710 can be inflated to increase the overall stent diameter $D_2$ and to engage the bladder 710 with the inner wall 372 (shown in FIG. 3) of the pipe 370. A fluid such as a gas (e.g., air) or a liquid can be pumped into the bladder 710 to inflate the bladder 710. In some aspects, the gas or liquid can be pumped into the bladder 710 through a channel 752 in the navigation stem 250. In other aspects, an onboard pump (not shown) mounted to the deployment probe 210 can be provided for inflating the bladder 710.

Figure 8:
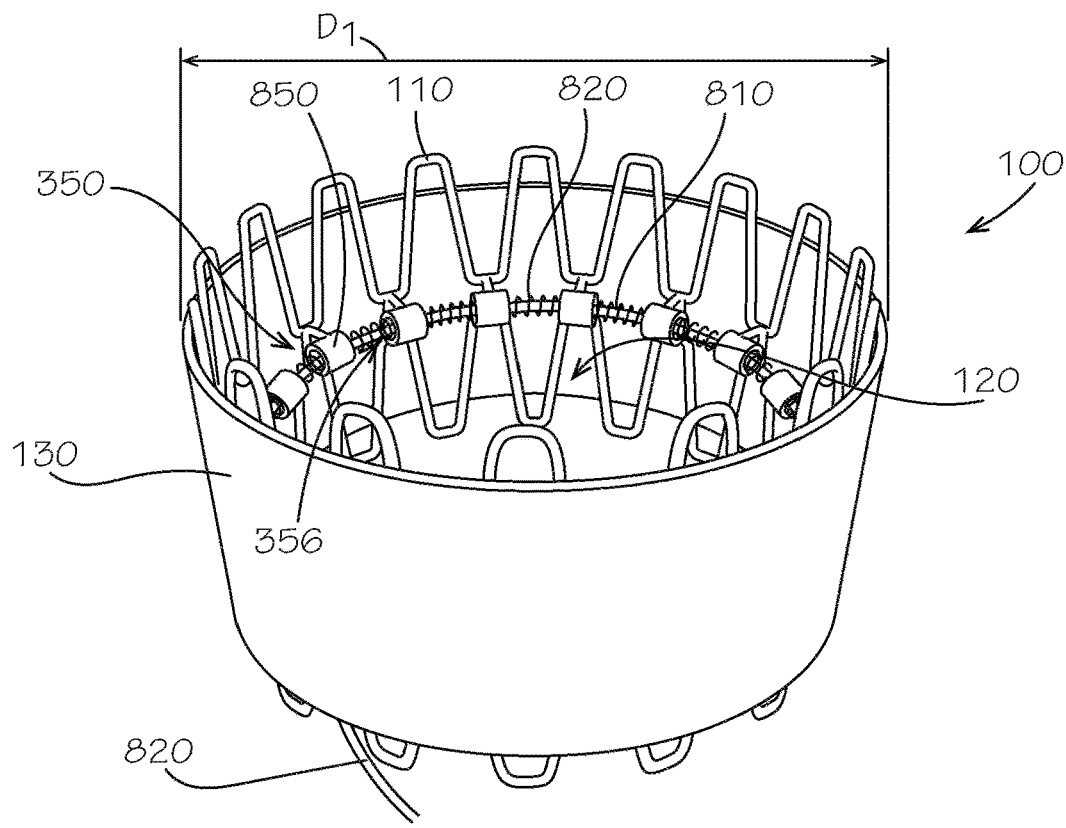
FIG. 8 is a top perspective view of the stent, according to another aspect of the present disclosure.

FIG. 8 illustrates another example aspect of the stent 100 comprising the stent spring 110 and the seal 130. In the present aspect, the engagement tabs 350 of the stent spring 110 are formed as hollow cylindrical structures 850 defining the tab opening 356 extending therethrough. In the present aspect, a coil spring 810 can extend through the tab openings 356, as shown. The coil spring 810 can define a coil spring force. In example aspects, like the stent spring 110, the coil spring 810 can be compressed in the compressed configuration and can be expanded in the expanded configuration. As described above, in the compressed configuration, a compression force, tension force, or other suitable force can be applied to the stent 100. For example, in the present aspect, a tension force can be applied by a cable 820. As shown, in the present aspect, the cable 820 can be configured to extend through a center of the coil spring 810. The cable 820 can be tightened such that a tension force of the cable 820 can overcome the spring force of the stent spring 110 and the coil spring force of the coil spring 810, such that the stent spring 110, coil spring 810, and seal 130 can be compressed or folded radially inward towards the stent void 120. When compressed, the stent 100 can define a smaller stent diameter $D_1$ and a smaller overall stent volume than in the expanded configuration. When the tension force is removed or reduced to less than the spring force and coil spring force, both of the stent spring 110 and the coil spring 810 can assist in biasing the stent 100 fully back to the expanded configuration. As such, in instances where one of the stent spring 110 and coil spring 810 may not bias the stent 100 fully back to the expanded configuration on its own, the other of the stent spring 110 and coil spring 810 can assist in further biasing the stent 100 towards the expanded configuration.

Figure 9:
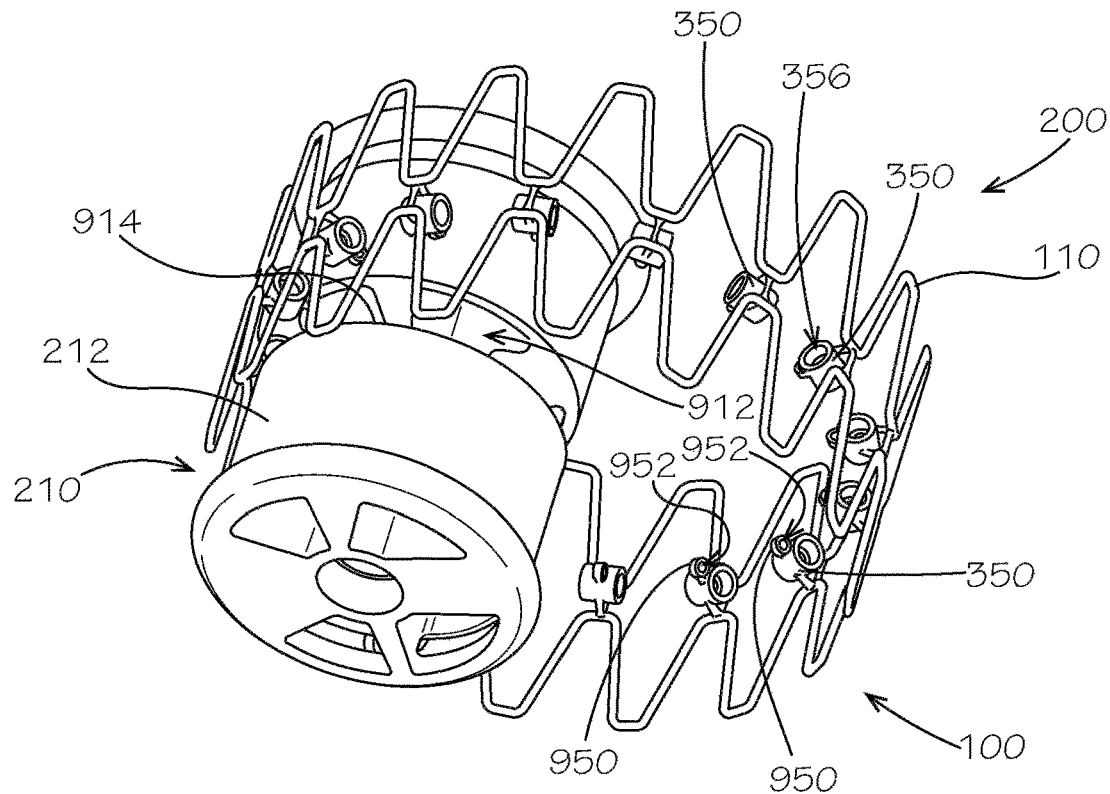
FIG. 9 is a top perspective view of the pipe repair assembly according to another aspect of the present invention.

FIG. 9 illustrates another example aspect of the pipe repair assembly 200. The pipe repair assembly 200 can comprise the stent 100 and the deployment probe 210, according to another aspect of the disclosure. As shown, the deployment probe 210 can be similar in size, shape, and structure to the deployment probe 210 of FIGS. 2-6. However, as shown in the present aspect, the deployment probe 210 may not define the slots 312 (shown in FIG. 3) formed in the probe body 212, and instead can define an annular groove 912 formed at about a center 914 of the probe body 212. The position of the annular groove 912 can correspond to the position of the engagement tabs 350 of the stent spring 110, such that the engagement tabs 350 can be received in the annular groove 912 when the stent spring 110 is mounted to the deployment probe 210 and the stent 100 is compressed. The stent spring 110 can be similar to the stent spring 110 of FIG. 8; however, in the present aspect, as shown, each of the engagement tabs 350 of the stent spring 110 can further define a loop 950 extending generally radially inward therefrom. Each of the loops 950 can define a loophole 952. According to example aspects, the cable 820 (shown in FIG. 8) can be configured to extend through the loopholes 952, instead of through the center of the coil spring 810 (shown in FIG. 8). When the cable 820 is tightened, the tension can draw the loops 950 radially inward, thus drawing the stent 100 inward to the compressed configuration.

Figure 10:
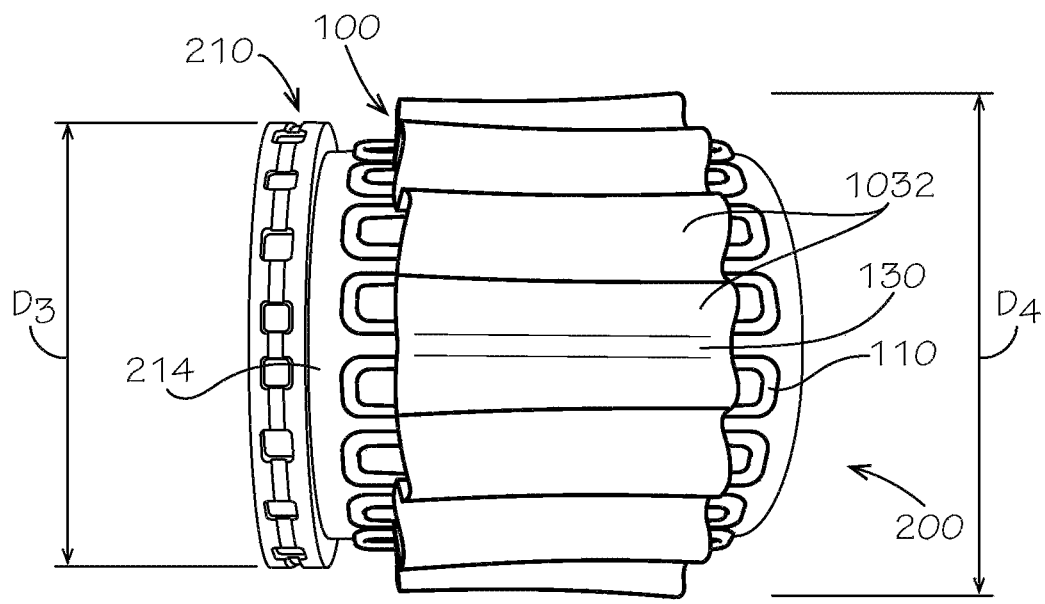
FIG. 10 illustrates the pipe repair assembly according to another aspect of the present invention, wherein the stent of FIG. 8 is in a compressed configuration.

FIG. 10 illustrates the stent 100 of FIG. 8 mounted to the deployment probe 210 in the compressed configuration. As shown, with the cable 820 (shown in FIG. 8) tightened, the stent 100 can be drawn radially inward to towards the deployment probe 210, such that the stent spring 110 can engage the outer surface 214 of the probe body 212. Furthermore, as shown, in the compressed configuration, the seal 130 can define a plurality of folds 1032. Optionally, the seal 130 can be configured such that a maximum diameter $D_4$ of the seal 130 in the compressed configuration can be about equal to or less than the maximum diameter $D_3$ of the deployment probe 210, to allow for easier passage of the pipe repair assembly 200 through the pipe 370 (shown in FIG. 3) and/or a pipeline. However, in other aspects, the maximum diameter $D_4$ of the seal 130 in the compressed configuration can be greater than the maximum diameter $D_3$ of the deployment probe 210.

Figure 11:
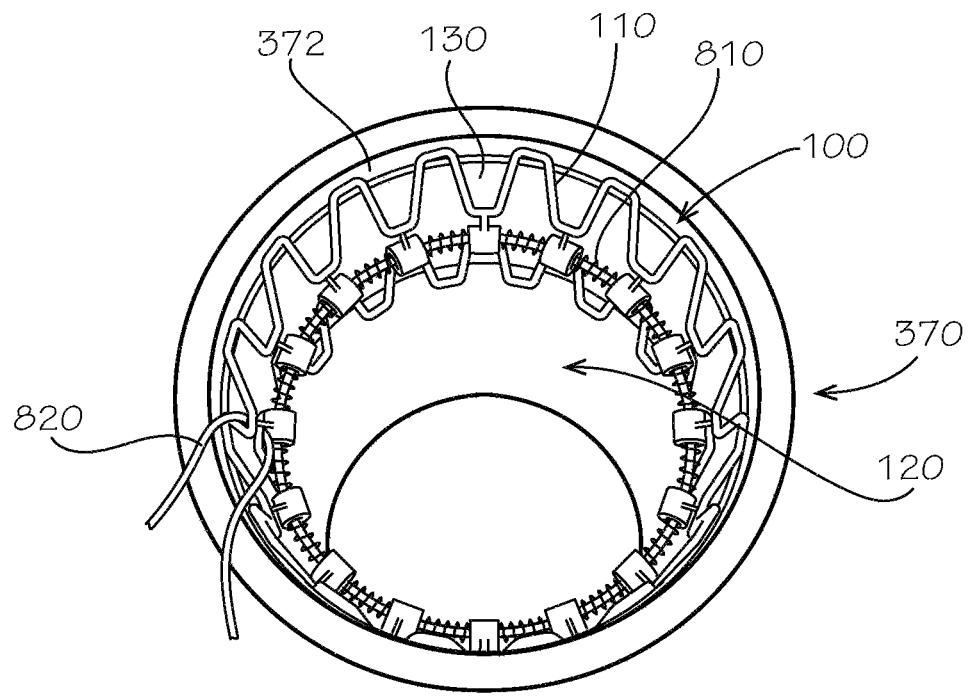
FIG. 11 illustrates the pipe repair assembly of FIG. 10, wherein the stent of FIG. 8 is in an expanded configuration.

FIG. 11 illustrates the stent 100 of FIG. 8 in the expanded configuration within the pipe 370 and with the deployment probe 210 (shown in FIG. 2) removed from the pipe 370.

According to example aspects, the stent 100 can be expanded within the pipe 370 such that the seal 130 can engage the inner wall 372 of the pipe 370 where a crack 374 (shown in FIG. 3) or other damage is present. The seal 130 can create a watertight seal between the stent 100 and the inner wall 372 of the pipe 370 to prevent leaking at the damage site. The stent 100 can be expanded by loosening the cable 820 to reduce or remove the tension force applied to the stent 100. With the tension force reduced, the spring force of the stent spring 110 and the coil spring force of the coil spring 810 can bias the stent 100 radially outward to the expanded configuration. The deployment probe 210 can be removed from the pipe 370 to allow fluid to flow freely through the stent void 120 of the stent 100. In some aspects, the cable 820 can be removed along with the deployment probe 210, while in other aspects, the cable 820 can remain connected to the stent 100, as shown.

Figure 12:
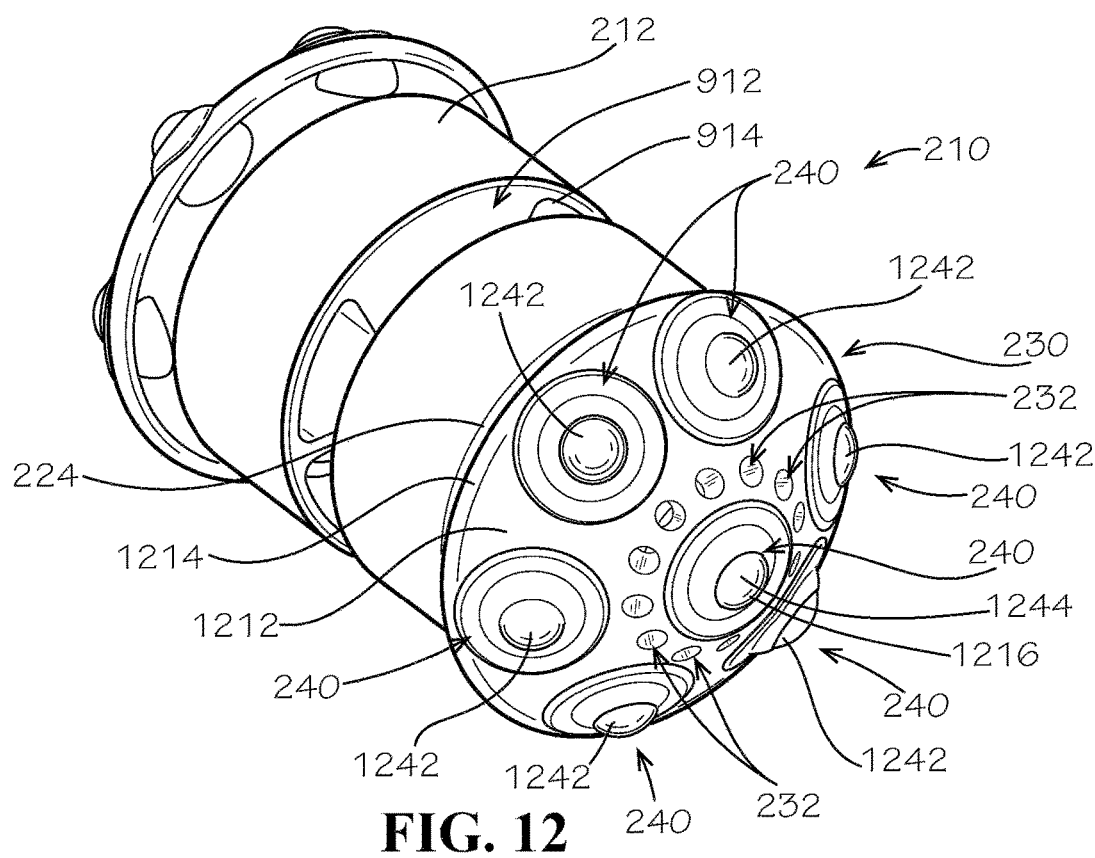
FIG. 12 is a front perspective view of the deployment probe according to another aspect of the present disclosure.

FIG. 12 illustrates a front perspective view of the deployment probe 210 according to another example aspect of the disclosure. Similar to the deployment probe 210 of FIG. 9, the deployment probe 210 of the present aspect can define the annular groove 912 formed at about the center 914 of the probe body 212. As described above, the annular groove 912 can be configured to receive the engagement tabs 350 (shown in FIG. 3) of the stent spring 110 (shown in FIG. 1). The deployment probe 210 can comprise the probe head 230 connected to the probe body 212 at the front end 224. In other aspects, the probe head 230 can be monolithically formed with the probe body 212. The one or more front openings 232 can be formed through the probe head 230 to allow fluid within the pipe 370 (shown in FIG. 3) to flow through the probe void 310 (shown in FIG. 3). The probe head 230 can also comprise the front ball bearings 240. In the present aspect, the front ball bearings 240 can be positioned on a front face 1212 of the probe head 230. For example, as shown, in one aspect, a plurality of outer front ball bearings 1242 can be positioned in a substantially circular pattern proximate an outer edge 1214 of the front face 1212, and an inner front ball bearing 1244 can be positioned substantially at a center 1216 of the front face 1212. As shown, the front openings 232 can be positioned in a substantially circular pattern on the front face 1212 between the outer front ball bearings 1242 and the inner front ball bearing 1244. In other aspects, the front ball bearings 240 and/or the front openings 232 can be positioned in any other suitable arrangement on the probe head 230. As described above, according to example aspects, the front ball bearings 240 can facilitate navigation of the pipe repair assembly 200 (shown in FIG. 2) through the pipe 370 or pipeline. For example, if one or more of the front ball bearings 240 contacts the inner wall 372 (shown in FIG. 3) of the pipe 370, the front ball bearing(s) 240 can roll along the inner wall 372, allowing the deployment probe 210 to move forward or rearward within the pipe 370.

Figure 13:
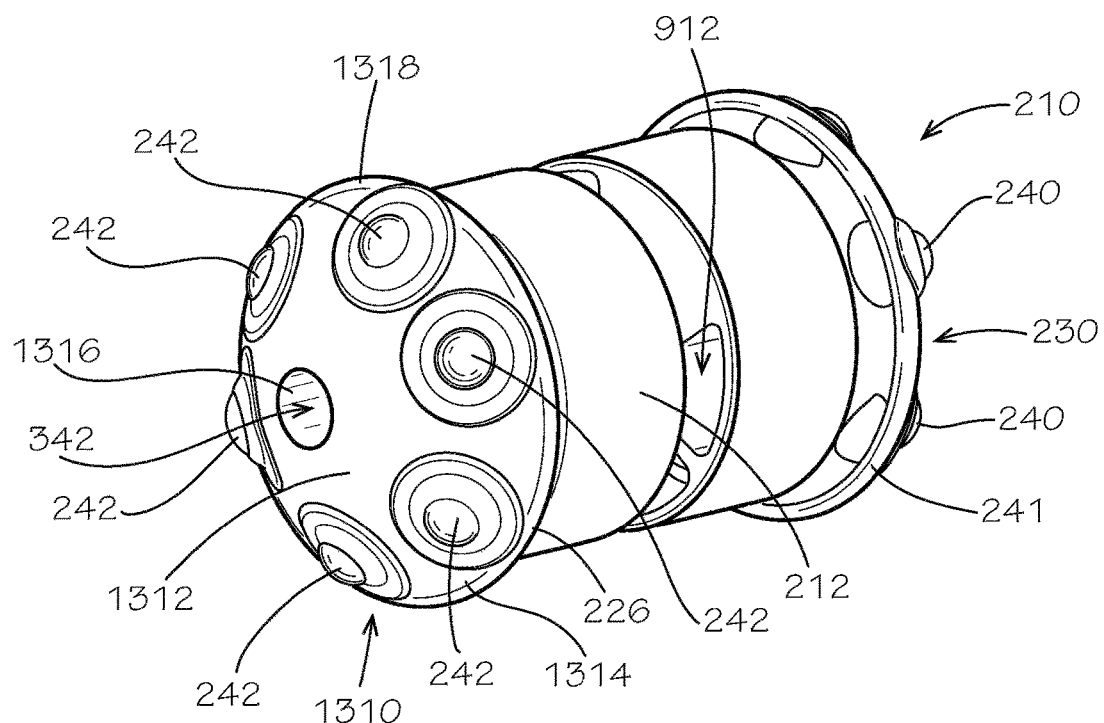
FIG. 13 is a rear perspective view of the deployment probe of FIG. 12.

FIG. 13 is a rear perspective view of the deployment probe 210 of FIG. 12. As shown, in the present aspect, the deployment probe 210 can define a rear cap 1310 connected to or monolithically formed with the probe body 212 at the rear end 226 thereof, opposite the probe head 230. A singular rear opening 342 can be formed through the rear cap 1310 to allow fluid within the pipe 370 (shown in FIG. 3) to flow all the way through the probe void 310 (shown in FIG. 3). As such, fluid in the pipe 370 can flow through the front openings 232 (shown in FIG. 12), into the probe void 310, and out of the rear opening 342, or vice versa. Other aspects can include additional rear openings 342. As shown, the rear cap 1310 can comprise the rear ball bearings 242. The rear ball bearings 242 can be positioned on a rear face 1312 of the rear cap 1310. For example, as shown, in one aspect, a plurality of the rear ball bearings 242 can be positioned in a substantially circular patter proximate an outer edge 1314 of the rear face 1312. Furthermore, the singular rear opening 342 can be formed at a center 1316 of the rear face 1312. In other aspects, the rear ball bearings 242 and/or the rear opening(s) 342 can be positioned in any other suitable arrangement on the rear cap 1310. Like the front ball bearings 240, the rear ball bearings 242 can also serve to facilitate navigation of the deployment probe 210 through the pipe 370 or pipeline.

In some aspects, the deployment probe 210 can comprise further navigation aiding devices (not shown). For example, in one aspect, one or more deflectors (not shown) can be positioned at or near the outer edge 1214 of the front face 1212 (shown in FIG. 12) of the probe head 230 and/or the outer circumference 241 of the probe head 230. One or more deflectors can also be positioned at or near the outer edge 1314 of the rear face 1312 of the rear cap 1310 and/or an outer circumference 1318 of the rear cap 1310. According to one example aspect, the deflectors can be formed as a flexible, resilient arch. During navigation, in instances wherein one or more of the deflectors engage the inner wall 372 (shown in FIG. 3) of the pipe 370 (shown in FIG. 3), the deflectors can be deformed upon contact with the inner wall 372. The resiliency of the deflectors can bias the deflector back to its original shape, pushing the deployment probe 210 away from inner wall 372 and allowing for easier navigation around bends and turns in the pipeline. In other aspects, the navigation aiding devices (not shown) can define any suitable configuration for facilitating navigation of the deployment probe 210 through the pipeline.

Figure 14:
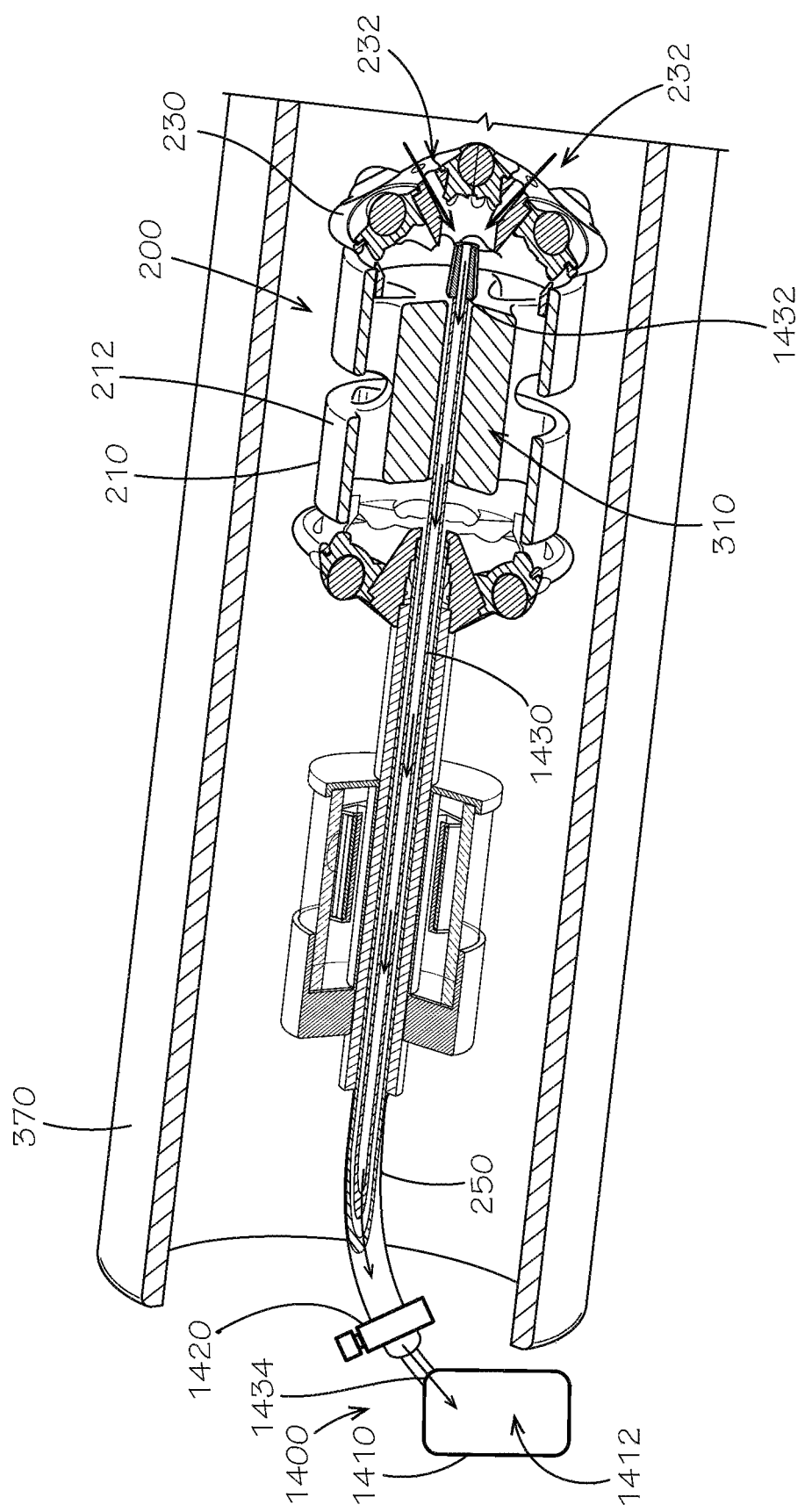
FIG. 14 is a cut-away view of the pipe repair assembly according to another aspect of the present disclosure.

FIG. 14 illustrates another aspect of the pipe repair assembly 200 deployed in the pipe 370. The pipe repair assembly 200 can comprise the deployment probe 210 and the stent 100 (shown in FIG. 1). In the present aspect, the pipe repair assembly 200 can further comprise a tank system 1400. The tank system 1400 can comprise a tank 1410 and a valve 1420, as shown, situated outside of the pressurized pipeline, and as such, an interior 1412 of the tank 1410 can be at atmospheric pressure. The tank 1410 can be connected to the deployment probe 210 by the navigation stem 250, which can define a fluid passageway 1430 formed therein. A front end 1432 of the fluid passageway 1430 can be oriented within the probe void 310 proximate the front openings 232 formed in the probe head 230, and a rear end 1434 of the fluid passageway 1430 can be oriented at the tank 1410. Example aspects of the valve 1420 can be selectively configured in a closed position and an open position. In the closed position, the valve 1420 can block the fluid passageway 1430, such that fluid cannot flow through the fluid passageway 1430 past the valve 1420. In the open position, the valve 1420 can unblock the fluid passageway 1430, such that a fluid (such as water) from inside the pipeline can flow into the fluid passageway 1430 through the front end 1432 thereof, past the valve 1420, and out of the rear end 1434 into the tank 1410. Because the tank 1410 is at atmospheric pressure and the fluid within the pipeline is pressurized, the fluid in the pipeline can be naturally drawn into and through the fluid passageway 1430 towards the tank 1410. As fluid is drawn through the front openings 232 in the probe head 230 and into the fluid passageway 1430, the pressure in the pipeline proximate the probe head 230 can drop. The reduced pressure at the probe head 230 can allow the deployment probe 210 to move forward through the pipe 370 with less resistance, which can be particularly useful in instances wherein the deployment probe 210 is moving forward against the fluid flow.

Figure 15:
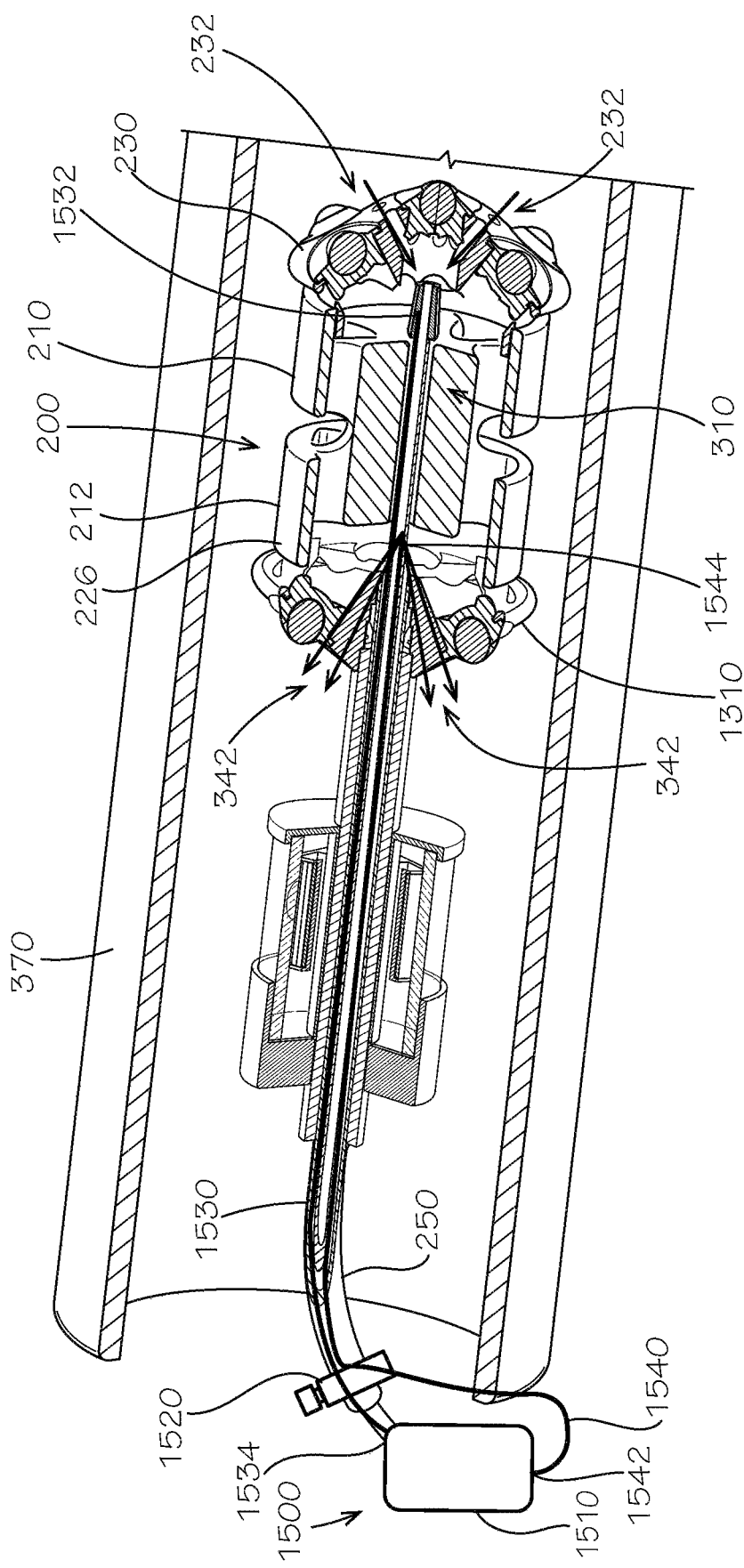
FIG. 15 is a cut-away view of the pipe repair assembly according to another aspect of the present disclosure.

FIG. 15 illustrates another aspect of the pipe repair assembly 200 deployed in the pipe 370. In the present aspect, the pipe repair assembly 200 can comprise a pump system 1500. The pump system 1500 can comprise an engine or motor (not shown), a pump 1510, and a valve 1520. The motor, the pump 1510, and the valve 1520 can be situated outside of the pressurized pipeline, as shown. The pump 1510 can be connected to the deployment probe 210 by an inlet passageway 1530 and a return passageway 1540, which in some instances, can be formed or partially formed within the navigation stem 250. A first end 1532 of the inlet passageway 1530 can be oriented within the probe void 310 proximate the front openings 232 formed in the probe head 230, and a second end 1534 of the inlet passageway 1530 can be oriented at the pump 1510. A first end 1542 of the return passageway 1540 can be oriented at the pump 1510, and a second end 1544 of the return passageway 1540 can be oriented proximate the rear openings 342 formed at the rear end 226 of the probe body 212 or in the rear cap 1310. Example aspects of the valve 1520 can be selectively configured in a closed position and an open position. In the closed position, the valve 1520 can block the inlet passageway 1530, such that fluid cannot flow through the inlet passageway 1530 past the valve 1520 and into the pump 1510. In the open position, the valve 1520 can unblock the inlet passageway 1530, such that a fluid (such as water) from inside the pipeline can flow into the inlet passageway 1530 through the first end 1532 thereof, past the valve 1520, and out of the second end 1534 into the pump 1510. The pump 1510 can then pump the fluid into the return passageway 1540 at the first end 1542 thereof, past the valve 1520, and out of the second end 1544. The fluid exiting the second end 1544 of the return passageway 1540 can be pushed out of the deployment probe 210 through the rear openings 342. Drawing the fluid into the inlet passageway 1530 proximate the probe head 230 can reduce the pressure in the pipeline proximate to the probe head 230, and pushing the fluid out of the return passageway 1540 proximate the rear openings 342 can increase the pressure in the pipeline proximate the rear cap 1310. The reduced pressure at the probe head 230 and increased pressure at the rear cap 1310 can allow the deployment probe 210 to move forward through the pipe 370 with less resistance, which can be particularly useful in instances wherein the deployment probe 210 is moving forward against the fluid flow.

Figure 16:
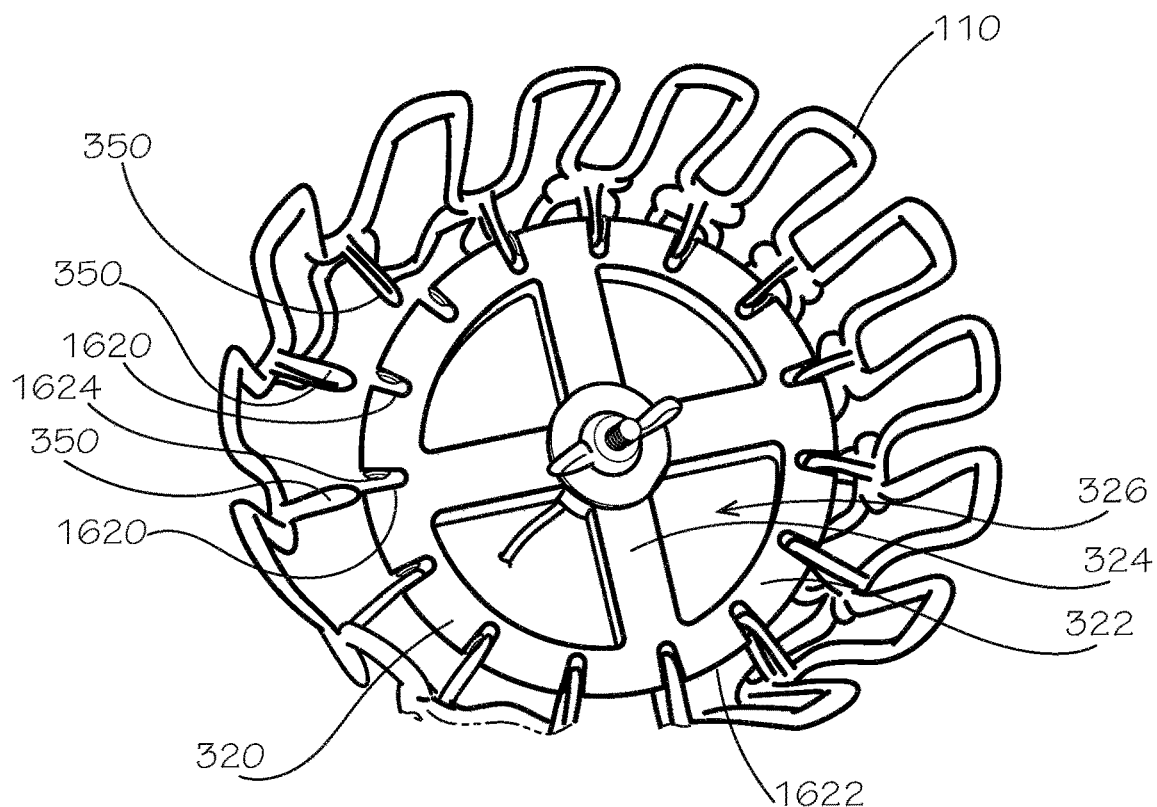
FIG. 16 is a top view of the release mechanism according to another aspect of the disclosure.
Figure 17:
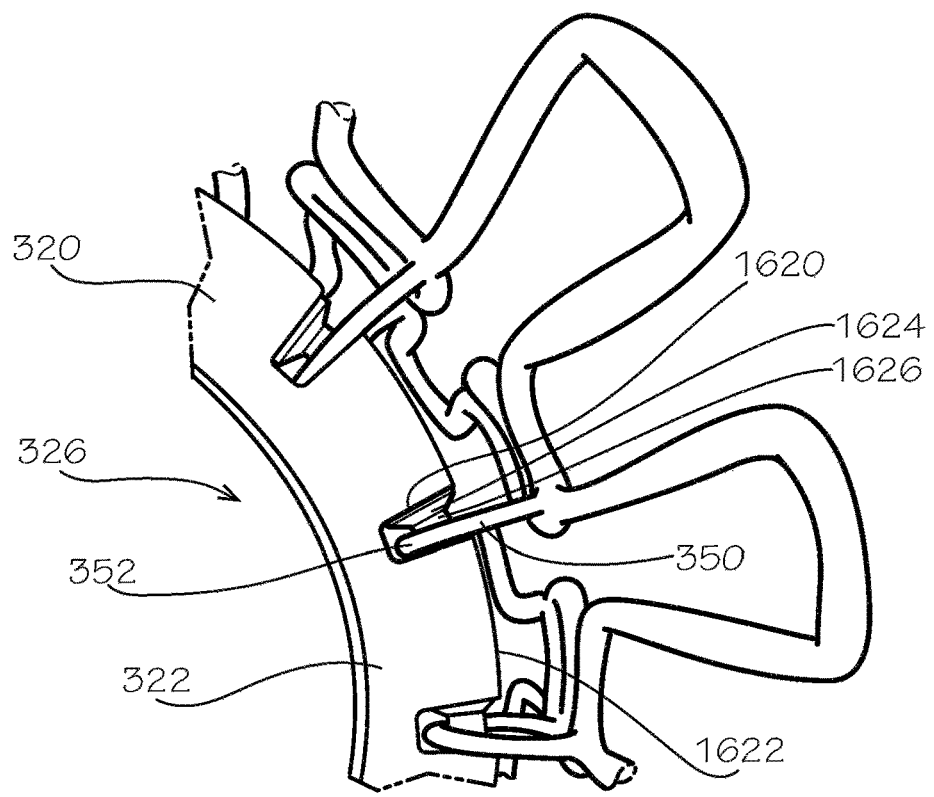
FIG. 17 is a close-up top view of the release mechanism of FIG. 16.
Figure 18:
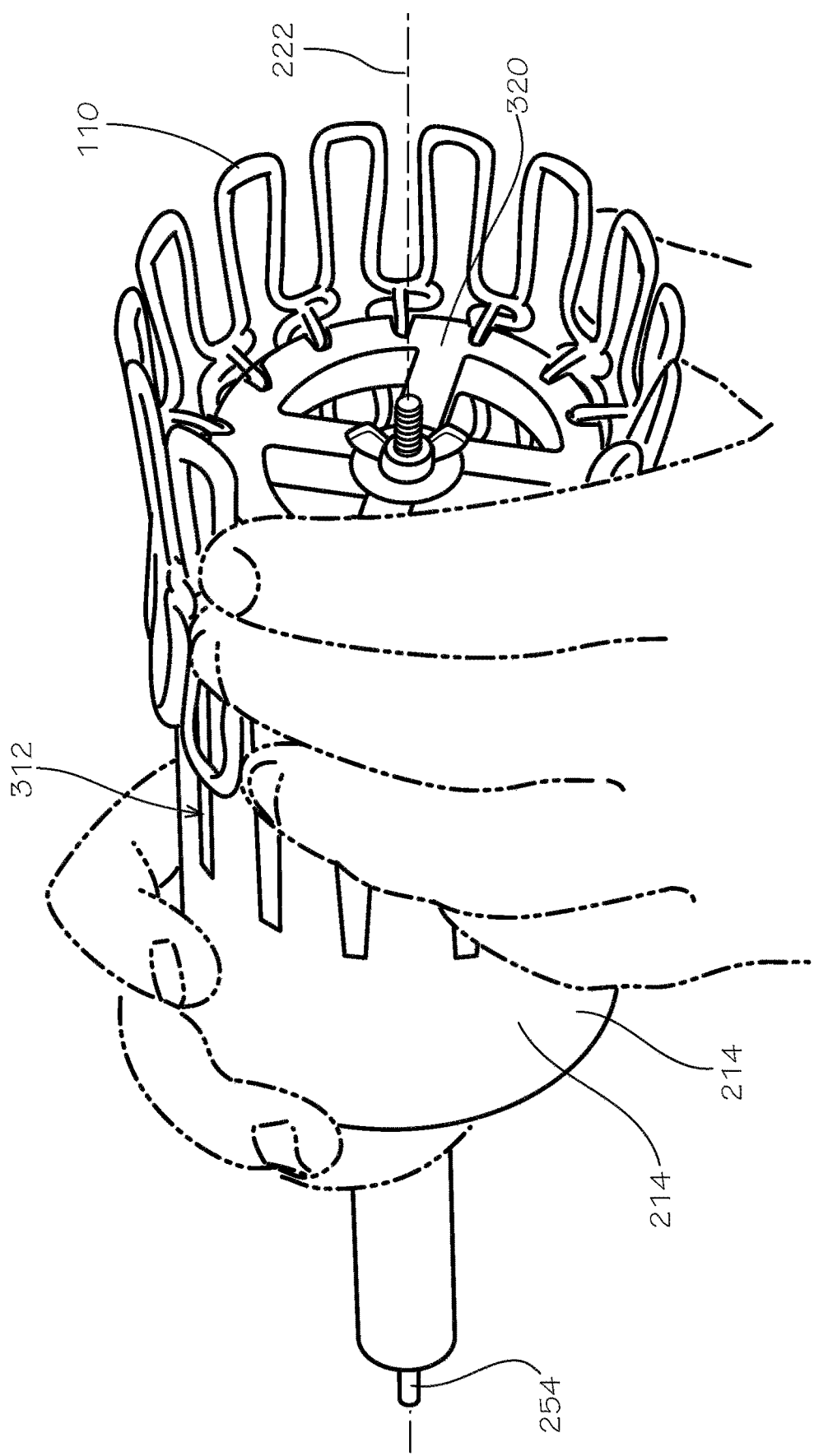
FIG. 18 is a side perspective view of the pipe repair assembly comprising the release mechanism of FIG. 16.

FIGS. 16 and 17 illustrate the stent spring 110 engaged with the release mechanism 320 according to another aspect. The release mechanism 320 can comprise the retainer body, such as the retainer wheel 322, as shown. The retainer wheel 322 can comprise the plurality of spokes 324, which can define the retainer wheel openings 326 therebetween to allow for the flow of fluid therethrough. Furthermore, one or more slots 1620 can be formed at an outer side edge 1622 of the retainer wheel 322. The retainer wheel 322, when mounted to the probe body 212 (as shown in FIG. 18), can be operatively connected to the release cable 254 (shown in FIG. 18). According to example aspects, the release mechanism 320 can be configured to engage each of the engagement tabs 350 of the stent spring 110 to pull the stent spring 110 radially inward and to retain the stent 100 (shown in FIG. 1) in the compressed configuration. The release mechanism 320 can comprise a plurality of the stent retainers, such as connectors 1624, positioned proximate to the outer side edge 1622 of the retainer wheel 322. A head 1626 (shown in FIG. 17) of each of the connectors 1624 can be configured to extend into a corresponding one of the slots 1620. To mount the stent spring 110 to the release mechanism 320 in the compressed configuration, the distal portion 352 of each of the engagement tabs 350 can be pushed radially inward past the head 1626 of the corresponding connector 1624 and into the corresponding slot 1620, such that the head 1626 of each connector 1624 extends through the tab opening 356 (shown in FIG. 3) of the corresponding engagement tab 350. With the head 1626 of each connector 1624 engaging a corresponding one of the engagement tabs 350, the stent spring 110 can be retained on the release mechanism 320 to orient the stent 100 in the compressed configuration.

Referring to FIG. 18, in the present aspect, once the stent 100 (shown in FIG. 1) is mounted to the release mechanism 320 by the connection of the stent spring 110 to the connectors 1624 (shown in FIG. 16), the stent 100 and the release mechanism 320 can be mounted together to the deployment probe 210. In other aspects, the release mechanism 320 may be mounted to the deployment probe 210 prior to mounting the stent 100 onto the release mechanism 320. Each of the engagement tabs 350 (shown in FIG. 3) of the stent spring 110 can be slid through a corresponding one of the slots 312, with the release mechanism 320 positioned within the probe void 310 (shown in FIG. 3) and the seal 130 (shown in FIG. 1) of the stent 100 generally wrapping around the outer surface 214 of the probe body 212. To move the stent 100 to the expanded configuration, the release mechanism 320 can be slid axially relative to the probe axis 222 by the release cable 254, as described above. The distal portion 352 (shown in FIG. 3) of each engagement tab 350 can be pushed past the heads 1626 (shown in FIG. 17) of the corresponding connectors 1624, such that each of the connectors 1624 can be disengaged from the corresponding tab opening 356 (shown in FIG. 3), and the release mechanism 320 can be disengaged from the stent spring 110. With the release mechanism 320 disengaged from the stent spring 110, the spring force of the stent spring 110 can bias the stent 100 to the expanded configuration.

One should note that conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment. It should be emphasized that the above-described embodiments are merely possible examples of implementations, merely set forth for a clear understanding of the principles of the present disclosure. Any process descriptions or blocks in flow diagrams should be understood as representing modules, segments, or sections of code which include one or more executable instructions for implementing specific logical functions or steps in the process, and alternate implementations are included in which functions may not be included or executed at all, may be executed out of order from that shown or discussed, including substantially concurrently or in reverse order, depending on the functionality involved, as would be understood by those reasonably skilled in the art of the present disclosure. Many variations and modifications may be made to the above-described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

That which is claimed is:

1. A deployment probe for deploying a stent comprising:
a probe body defining a front end, a rear end, an inner surface, an outer surface, and a slot extending from the inner surface to the outer surface, the inner surface defining a probe void, the probe void defining a probe axis, the slot extending in an axial direction relative to the probe axis; and
a release mechanism comprising a retainer body received within the probe void and a stent retainer coupled to the retainer body, the stent retainer substantially aligned with the slot and configured to engage a stent;
a probe head arranged at the front end of the probe body and extending substantially radially inward from the probe body, at least one front opening formed through the probe head, the at least one front opening oriented radially inward of the inner surface of the probe body and allowing fluid to flow into the probe void in a substantially axial direction.

2. The deployment probe of claim 1,
further comprising at least one rear opening formed at the rear end, the at least one rear opening oriented radially inward of the inner surface of the probe body and allowing fluid to flow out of the probe void in a substantially axial direction.

3. The deployment probe of claim 1, wherein the probe head comprises one or more ball bearings.

4. The deployment probe of claim 1, wherein the retainer body is a retainer wheel, the retainer wheel comprising a plurality of radially extending spokes, the spokes defining retainer wheel openings therebetween.

5. The deployment probe of claim 1, wherein the release mechanism is axially movable within the probe void between an engaged position and a disengaged position.

6. The deployment probe of claim 5, further comprising a release cable, the release cable operatively coupled to the release mechanism to move the release mechanism between the engaged position and the disengaged position.

7. The deployment probe of claim 1, wherein the stent retainer is a retainer clip, the retainer clip comprising a first spring leg and a second spring leg, the first spring leg and second spring leg bent towards one another to define a pinched middle section of the retainer clip.

8. The deployment probe of claim 1, wherein:
a slot is formed at an outer side edge of the retainer body; and
the stent retainer is a connector comprising a head extending into the slot.

9. The deployment probe of claim 1, wherein the front end of the probe body is an axially front end and the rear end of the probe body is an axially rear end, and wherein the axially rear end is axially spaced from the axially front end, relative to the probe axis.

10. The deployment probe of claim 9, wherein the probe head defines a diameter that is greater than a diameter of the probe body.

11. The deployment probe of claim 10, further comprising a rear cap arranged at the rear end of the probe body, the rear cap defining a diameter that is greater than the diameter of the probe body.

12. The deployment probe of claim 9, wherein the probe head defines an axially inner surface and an axially outer surface, the axially outer surface axially spaced from axially inner surface, the front opening extending from the axially outer surface to the axially inner surface.

* * * * *